United States Patent
Mullen et al.

(10) Patent No.: US 9,944,584 B2
(45) Date of Patent: Apr. 17, 2018

(54) METHOD FOR REMOVING MINERAL ACID FROM LEVULINIC ACID

(71) Applicant: GFBiochemicals Limited, Valletta (MT)

(72) Inventors: Brian D. Mullen, Delano, MN (US); Vivek Badarinarayana, St. Louis Park, MN (US)

(73) Assignee: GFBIOCHEMICALS LIMITED (MT)

( * ) Notice: Subject to any disclaimer, the term of this patent is extended or adjusted under 35 U.S.C. 154(b) by 0 days.

(21) Appl. No.: 15/123,520

(22) PCT Filed: Mar. 2, 2015

(86) PCT No.: PCT/US2015/018235
§ 371 (c)(1),
(2) Date: Sep. 2, 2016

(87) PCT Pub. No.: WO2015/134352
PCT Pub. Date: Sep. 11, 2015

(65) Prior Publication Data
US 2016/0368850 A1    Dec. 22, 2016

Related U.S. Application Data

(60) Provisional application No. 61/947,185, filed on Mar. 3, 2014.

(51) Int. Cl.
*C07C 59/00* (2006.01)
*C07C 51/48* (2006.01)
*B01D 11/04* (2006.01)

(52) U.S. Cl.
CPC .......... *C07C 51/48* (2013.01); *B01D 11/0426* (2013.01); *B01D 11/0492* (2013.01)

(58) Field of Classification Search
CPC .. C07C 51/48; C07C 59/185; A61M 15/0091; A61M 15/06; A61M 16/20; A61M 2202/0468; A61M 2209/045; H01M 4/8652; H01M 4/8657; H01M 4/9016; H01M 4/9041; H01M 4/92; H01M 8/10; A24B 15/16; A24F 47/002; A24F 47/006; B65D 83/42; B65D 83/425; B65D 83/48; B65D 83/752; Y02E 60/50; B01D 11/0426; B01D 11/0492; B65C 83/48
See application file for complete search history.

(56) References Cited

U.S. PATENT DOCUMENTS

| 2,614,031 A | * | 10/1952 | Tickler | B01D 11/043 196/14.52 |
| 2012/0302765 A1 | * | 11/2012 | Dumesic | C07D 307/50 549/326 |
| 2012/0302766 A1 | * | 11/2012 | Dumesic | C07C 51/48 549/326 |
| 2013/0331601 A1 | | 12/2013 | Tirronen et al. | |

FOREIGN PATENT DOCUMENTS

| WO | WO 2010/030617 A1 | 3/2010 |
| WO | WO 2012/162028 | 11/2012 |
| WO | WO2013/078391 | * 5/2013 |
| WO | WO 2014/189991 | 11/2014 |

OTHER PUBLICATIONS

Supplementary European Search Report issued in European Application No. 15758345, dated Dec. 1, 2017.

* cited by examiner

*Primary Examiner* — Yevgeny Valenrod
*Assistant Examiner* — Blaine G Doletski
(74) *Attorney, Agent, or Firm* — Norton Rose Fulbright US LLP

(57) ABSTRACT

The invention describes processes to selectively remove or reduce the mineral acid content substantially from compositions comprising a solvent and levulinic acid, wherein the levulinic acid was derived from the reaction between various biomass materials and a mineral acid or an organic acid catalyst.

11 Claims, 1 Drawing Sheet

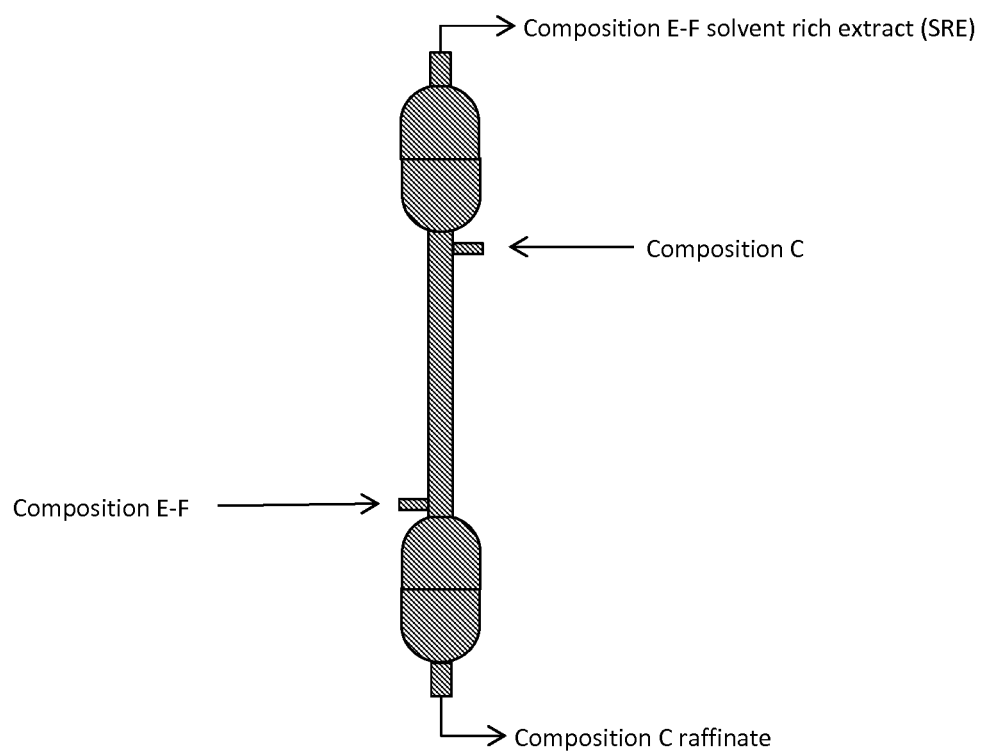

METHOD FOR REMOVING MINERAL ACID FROM LEVULINIC ACID

CROSS REFERENCE TO RELATED APPLICATIONS

This application is a national phase application under 35 U.S.C. § 371 of International Application No. PCT/US2015/018235, filed Mar. 2, 2015, which claims priority to U.S. Provisional Patent Application No. 61/947,185, filed Mar. 3, 2014. The entire contents of each of the above-referenced disclosures are specifically incorporated herein by reference without disclaimer.

FIELD OF THE INVENTION

The invention relates generally to the removal of mineral acid(s) from levulinic acid that are present as a result from the processes to prepare levulinic acid.

BACKGROUND OF THE INVENTION

Levulinic acid ("LA") can be used to make resins, plasticizers, specialty chemicals, herbicides and as a flavor substance. Levulinic acid is useful as a solvent, and as a starting material in the preparation of a variety of industrial and pharmaceutical compounds such as diphenolic acid (useful as a component of protective and decorative finishes), calcium levulinate (a form of calcium for intravenous injection used for calcium replenishment and for treating hypocalcemia. The use of the sodium salt of levulinic acid as a replacement for ethylene glycols as an antifreeze has also been proposed.

Esters of levulinic acid are known to be useful as plasticizers and solvents, and have been suggested as fuel additives. Acid catalyzed dehydration of levulinic acid yields alpha-angelica lactone.

Levulinic acid has been synthesized by a variety of chemical methods. But levulinic acid has not attained much commercial significance due in part to the high cost of the raw materials needed for synthesis. Another reason is the low yields of levulinic acid obtained from most synthetic methods. Yet, another reason is the formation of a formic acid byproduct during synthesis and its separation from the levulinic acid. Therefore, the production of levulinic acid has had high associated equipment costs. Despite the inherent problems in the production of levulinic acid, however, the reactive nature of levulinic acid makes it an ideal intermediate leading to the production of numerous useful derivatives.

Cellulose-based biomass, which is an inexpensive feedstock, can be used as a raw material for making levulinic acid. The supply of sugars from cellulose-containing plant biomass is immense and replenishable. Most plants contain cellulose in their cell walls. For example, cotton comprises 90% cellulose. Furthermore, it has been estimated that roughly 75% of the approximate 24 million tons of biomass generated on cultivated lands and grasslands are waste. The cellulose derived from plant biomass can be a suitable source of sugars to be used in the process of obtaining levulinic acid. Thus, the conversion of such waste material into a useful chemical, such as levulinic acid, is desirable.

In the synthesis of levulinic acid (LA) from carbohydrates, the reactions are typically performed in the presence of water and strong mineral acids, like sulfuric acid (SA). After the levulinic acid is synthesized, it has to be efficiently and selectively removed from the aqueous mineral acid mixture. Perhaps one of the most practical methods utilizes liquid liquid extraction to extract the LA into an organic solvent. Liquid-liquid extraction is efficient for extracting levulinic acid, but it is not completely selective with regards to extracting levulinic acid and not extracting sulfuric acid. Thus, sulfuric acid is extracted into the organic extraction solvent with the levulinic acid. Sulfuric acid can be problematic during subsequent purification steps because it can help catalyze side reactions of levulinic acid and the extraction solvent.

After extraction of LA from the solvent, the solvent must be purified by distillation at moderate to high temperatures and then, optionally, recycled back into the process in order for the process to be practical economically. However, if sulfuric acid is not removed appreciably from the organic extraction solvent containing LA, then there are considerable yield losses of the extraction solvent and LA due to side reactions that can be catalyzed by mineral acid.

Thus, a need exists for a method to remove sulfuric acid or minimize the amount of sulfuric acid present in the organic extraction solvent and LA in order to prevent or minimize side reactions of the organic extraction solvent and LA.

BRIEF SUMMARY OF THE INVENTION

A major issue in producing levulinic acid is the separation of pure levulinic acid from acidic byproducts, especially from formic acid, char and the reaction catalyst, a mineral acid, used in the preparation of the levulinic acid. Current processes generally require high temperature reaction conditions, generally long digestion periods of biomass, use of mineral acid(s) catalysts, specialized equipment to withstand hydrolysis conditions, and as a result, the yield of the levulinic acid can be quite low, generally in yields of 30 percent or less.

A method to prepare a levulinic acid composition substantially without mineral acid present is presented. The method includes the steps of providing a levulinic acid composition comprising levulinic acid, a mineral acid and an organic solvent; treating the levulinic acid composition with an aqueous solution comprising a monosaccharide, a disaccharide or mixtures thereof, to form a mixture; and partitioning the mixture into an aqueous phase and an organic phase, wherein the mineral acid in the organic phase is reduced relative to the amount in the levulinic acid composition.

In another aspect, a continuous counter current liquid liquid extraction process to prepare levulinic acid compositions with substantially reduced mineral acid is provided. The process includes providing a levulinic acid composition comprising levulinic acid, a mineral acid and an organic solvent; flowing the levulinic acid composition into a bottom inlet of a counter current liquid liquid extractor; providing an aqueous solution comprising water and one or more monosaccharides, disaccharides or mixtures thereof; flowing the aqueous solution into an upper inlet of a counter current liquid liquid extractor; and removing a resultant organic solvent rich extract containing levulinic acid with reduced amounts of mineral acid relative to the mineral acid content of the levulinic acid composition.

In another aspect of the invention, recovery of levulinic acid by distillation was accomplished, in which a reduced amount of LA-solvent byproducts was formed when the inventive method was utilized prior to distillation.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 1 is an illustration of liquid-liquid extraction column used for extraction of sulfuric acid from compositions E and F described herein.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention provides various advantages in the isolation of levulinic acid (LA), formic acid (FA) and/or hydroxymethyl furfural (HMF) and separation or removal of mineral acid from an extraction solvent that includes LA and the mineral acid. The following list of advantages is not meant to be limiting but highlights some of the discoveries contained herein.

Processes to Prepare Levulinic Acid

Methods to convert biomass as an initial feedstock to prepare the levulinic acid, hydroxymethyl furfural and/or formic acid are known. For example, levulinic acid has been prepared by conversion of biomass as described in WO/2013/078391 and U.S. 61/887,657, the contents of which are incorporated herein in their entirety. In general, an aqueous mixture of a biomass and a mineral acid are heated for a period of time to produce levulinic acid and other products. The mixture is cooled and the aqueous phase containing the levulinic acid is separated from any remaining solids. The aqueous phase is then extracted with a solvent or the water is removed by distillation. Recovered LA can then be further purified by crystallization, distillation, chromatography, or other methods known in the art. This ability to utilize a wide variety of biomass provides great flexibility in obtaining a constant source of starting material and is not limiting. However, residual mineral acid from the preparation process causes degradation of the LA, produces unwanted byproducts and/or char.

Biomass comprises sludges from paper manufacturing process; agricultural residues; bagasse pitt; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water; post-fermentation liquor; furfural still residues; and combinations thereof, furfuryl alcohol, a C5 sugar, a C6 sugar, a lignocelluloses, cellulose, starch, a polysaccharide, a disaccharide, a monosaccharide or mixtures thereof. Preferably the biomass is high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof, and more preferably, the biomass comprises fructose, glucose or a combination thereof.

Biomass can be a refined material, such as fructose, glucose, sucrose, mixtures of those materials and the like. As such, there is a plentiful supply of materials that can be converted into the ultimate product(s). For example, sugar beets or sugar cane can be used as one source. Fructose-corn syrup is another readily available material. Use of such materials thus helps to reduce the costs to prepare desired products, such as levulinic acid.

In the production of levulinic acid, use of high concentrations of acid(s), generally about 20 weight percent or more (based on the total mass of the reaction medium) provides a cleaner reaction product with less char and unwanted byproducts. It has also been found that use of high concentrations of acid(s), generally up to 75 weight percent or more, (based on the total mass of the reaction medium) provides faster reaction times than lower acid concentrations used with the same reaction conditions. However, the use of increased concentration of acid(s) results in increased levels of such acids in extraction solvents used to partition the LA.

Also, in the production of levulinic acid, when higher concentrations of acid are utilized in the conversion of biomass to levulinic acid, etc., the reaction conditions can be conducted at much lower temperatures than are currently utilized in the literature. This approach lessens the amount of byproducts from the reaction(s) that take place and increases the yield of the desired product(s). Again, however, the use of increased concentration of acid(s) results in increased levels of such acids in extraction solvents used to partition the LA.

Acid Catalysts

Suitable acid catalysts used to convert the biomass materials described herein, including sugars, include mineral acids, such as but not limited to sulfuric acid, hydrochloric acid, hydrobromic acid, hydroiodic acid, and organic acids, such as but not limited to methane sulfonic acid, p-toluene sulfonic acid, perchloric acid and mixtures thereof. It should be understood that where the discussions are directed to a particular acid catalyst, that the use of the term is exemplary and is applicable to any of the acid catalysts described herein. It should also be understood that levulinic acid and formic acid, generated during some of the processes are not considered as "acid catalysts" for the embodiments described herein.

Flash

The reaction products of the levulinic acid process may be optionally cooled in a "flash" process. The flash step rapidly cools the reaction products by maintaining a pressure low enough to evaporate a significant fraction of the products. This pressure may be at or below atmospheric pressure. The evaporated product stream may be refluxed through stages of a distillation column to minimize the loss of desired reaction products, specifically levulinic acid, and to ensure recovery of formic acid reaction products and solvent. Recovered solvent may be recycled back to the reactor.

The "bottoms" or less volatile stream from the flash step can be advanced to a solids separation stage.

Solids Separation

In the solids separation stage of the process, the solvent and desired reaction product, specifically levulinic acid, is separated from any char which may have formed during the reaction phase. The char may be separated through a combination of centrifuge, filtration, and settling steps (ref Perrys Chemical Engineering Handbook, Solids Separation). The separated solids may be optionally washed with water and solvents to recover desired reaction products or solvent which may be entrained in or adsorbed to the solids. It has been found that in some embodiments, such as those reactions employing high levels of mineral acid (greater than 20%) that are reacted at lower temperatures, such as between 60-110° C., the solids may have density properties similar to the liquid hydrolysate which effectively allows the solids to be suspended in solution. In these embodiments, certain separation techniques such as centrifugation are not as effective. In these embodiments filtration utilizing filter media having a pore size less than about 20 microns has been found to effectively remove solids from the mixture. When removing solids from the system a solid "cake" is formed. It is desirable that the cake be up to 50% solids. Thus any separation technique that obtains a cake having a higher amount of solids is preferred. A certain amount of LA and mineral acid will be present in the cake and it may be desirable to wash the cake with an extraction solvent or water to recover LA.

Solid particles in the high mineral acid and lower temperature embodiments are easily filtered and do not inhibit flow as the cake is formed. It is believed that the properties of the char formed under these process conditions are such that any cake remains porous enough that a small filter size (less than 20 microns) can be utilized while maintaining a high flow rate through the medium.

It has been found efficacious to treat the biomass material(s) in an aqueous environment with a water immiscible solvent. Not to be limited by theory, it is believed that the partitioning of the starting materials from the product(s) between the aqueous and non-aqueous layers provides for one or more of: increased yield, reduced charring and/or by-products, faster reaction times and reduced reaction temperatures. However, the water immiscible solvents do not completely partition all mineral acid from the solvent itself and/or LA.

Under low acid conditions, high temperature is required to effectively hydrolyze the sugar in a reasonable time frame. When small amounts of sulfuric acid are used, the strong inorganic acid can effectively be neutralized to its salt form by careful addition of stoichiometric amounts of base. When high acid concentrations are used, the quantity of salt produced would be excessive. Likewise, the use of an ion exchange column is impractical because the large quantity of inorganic acid would quickly fill the capacity of the column.

Solvent extraction techniques, where the organic acids are preferably extracted into an organic solvent, are preferred. However, the high acid catalyst, e.g., mineral acid, content poses challenges. The organic solvent should be insoluble in the aqueous phase, but in some cases, the acid catalyst, such as sulfuric acid, can affect compatibility of the organic solvent and the aqueous phase. When this happens, a portion of the organic solvent becomes soluble in the concentrated acid catalyst, e.g., sulfuric acid aqueous phase, and the risk of solvent loss to side reactions increases. Even if the organic solvent is stable in the aqueous acid catalyst, e.g., sulfuric acid, phase, the organic solvent must be recovered from the aqueous stream for recycling to the extraction unit for optimized economics. High acid catalyst, e.g., mineral acid, concentration also carries with it the potential for higher acid catalyst, e.g., mineral acid, concentrations in the organic phase. When this happens, there is the risk of solvent loss to side reactions with the acid catalyst.

In one embodiment, the partition coefficient of the extraction solvent for levulinic acid is at least 0.3, more specifically, at least 0.5, more specifically, at least 0.7, more specifically, at least 1.0, more specifically at least 1.3, more specifically, at least 1.5 more specifically, at least 1.7, and more specifically at least 2.0. In one embodiment, the partition coefficient of the extraction solvent for formic acid is at least 0.3, more specifically, at least 0.5, more specifically, at least 0.7, more specifically, at least 1.0, more specifically at least 1.3, more specifically, at least 1.5 more specifically, at least 1.7, and more specifically at least 2.0, more specifically, at least 2.3, more specifically, at least 2.5, more specifically, at least 3.0, more specifically, at least 3.5, more specifically, at least 4.0, more specifically, at least 5.0 more specifically, at least 6.0, more specifically, at least 7.0, more specifically, at least 8.0, and more specifically, at least 9.0.

Suitable extraction solvents are presented below.

Removal of Acid Catalyst(s) from Levulinic Acid

The selective removal of trace amounts of acid catalysts, e.g., mineral acids, in the presence of levulinic acid has not been described previously. As described herein, the selective removal of an acid catalyst, e.g., a mineral acid, is accomplished by back-washing an organic extraction solvent comprising levulinic acid and, for example, a mineral acid such as sulfuric acid, with an aqueous solution comprising a monosaccharide, a mixture of monosaccharides, a disaccharides, a mixture of disaccharides or mixtures of monosaccharide(s) and disaccharide(s). The method selectively removes the acid catalyst from the organic solvent containing the levulinic acid and improves the levulinic acid to acid catalyst weight ratio by at least greater than 2× (2 times), and preferably by an order of magnitude. By reducing the acid catalyst to these lower levels, detrimental acid-catalyzed side reactions of levulinic acid and the organic solvent are prevented.

Extraction Solvents

Suitable solvents to extract LA include, for example, polar water-insoluble solvents such as methyl-isobutyl ketone (MIBK), methyl isoamyl ketone (MIAK), cyclohexanone, o, m, and para-cresol, substituted phenols, for example, 2-sec butyl phenol, C4-C18 alcohols, such as n-pentanol, isoamyl alcohol, n-heptanol, 2-ethyl hexanol, n-octanol, 1-nonanol, cyclohexanol, methylene chloride, 1,2-dibutoxy-ethylene glycol, acetophenone, isophorone, o-methoxy-phenol, methyl-tetrahydrofuran, tri-alkylphosphine oxides (C4-C18)

and ortho-dichlorobenzene and mixtures thereof or the like, more specifically, methyl isoamyl ketone (MIAK), o, m, and para-cresol, phenol, isoamyl alcohol, n-hexanol, n-heptanol, 2-ethyl hexanol, o-methoxy-phenol, 2-4 dimethyl phenol, methyl isobutyl carbinol, and mixtures thereof or the like, and even more specifically, phenol, all isomers of fluoro, chloro, bromo, and iodo phenols, bis-halogenated phenols, mixtures of halogenated phenols, xylenols, gamma-valerolactone, isoamyl alcohol, neopentyl alcohol, methyl isobutyl carbinol, and mixtures thereof or the like. Such solvents are used generally at room temperature so as not to serve as potential reaction component.

Concentration of LA in the organic phase/extraction solvent varies from about 1% to about 30% by weight, more particularly from about 2% to about 25% and even more particularly from about 3% to about 20% by weight.

As noted above, the extraction solvent/LA includes a percentage of an acid catalyst, e.g., a mineral acid that is sought to be removed. Typically, the concentration of the acid catalyst, e.g., a mineral acid, present in the extraction solvent is from about 0.01% to about 5% by weight based on the total weight of the organic solvent comprising the levulinic acid.

In one aspect, the amount of acid catalyst left in the isolated levulinic acid is less than 500 ppm, more particularly, less than 400 ppm, less than 300 ppm, less than 200 ppm, less than 100 ppm, less than 75 ppm, less than 50 ppm, less than 25 ppm, less than 10 ppm, less than 9 ppm, less than 8 ppm, less than 7 ppm, less than 6 ppm, less than 5 ppm, less than 4 ppm, less than 3 ppm, less than 2 ppm, or less than 1 ppm as measured by ion chromatograph. In one embodiment, the acid catalyst cannot be detected by ion chromatography.

Aqueous Wash/Treatment Solutions

The organic phase, noted above, that contains LA and residual mineral acid is treated with an aqueous treatment solution to partition the mineral acid into the aqueous phase, thus reducing the mineral acid concentration in the organic phase by at least an order or magnitude.

Suitable aqueous wash solutions contain one or more monosaccharides, one or more disaccharides or mixtures of a monosaccharide(s) and a disaccharide(s). Suitable monosaccharides include, for example, glucose, fructose or mixtures thereof. Suitable disaccharides include, for example, sucrose, maltose or mixtures thereof. Concentration of the monosaccharide or disaccharide in the aqueous wash solutions can vary from about 5% to about 80% by weight, more particularly from about 10% to about 40% and even more particularly from about 15% to about 30% by weight.

Separation of aqueous phase (with extracted mineral acid) from organic extraction phase (comprising LA) may be accomplished by settling, decanting, or centrifugation.

Solvent Removal

Levulinic acid may be separated from the solvent phase by evaporating or distilling the solvent. Alternatively, the levulinic acid may be crystallized from the solvent phase in a crystallization process. The solvent removal process may be a combination of distillation and crystallization. The recovered solvent may be recycled to the extraction step or to other steps.

The resulting stream of highly concentrated levulinic acid may be advanced for further chemical derivatization or may be further purified in another distillation step such as high vacuum wipe-film-evaporation or falling film evaporation. Preferably the levulinic acid stream is kept at a low temperature throughout the solvent removal steps to inhibit the formation of angelica lactone.

Alternatively, the LA may be separated from the solvent by selective adsorption of the LA or the solvent onto a solid phase material. The solid phase material may be inert or reactive (anion exchange resin).

Alternatively, the LA may be reacted with a C1-C18 primary alcohol to form an ester, and the ester may be separated from the solvent by distillation or crystallization.

The following paragraphs, numbered 1 through 21 provide for various aspects of the present embodiments. In one embodiment, in a first paragraph (1), method to prepare a levulinic acid composition substantially without an acid catalyst present comprising the steps:

providing a levulinic acid composition comprising levulinic acid, an acid catalyst and a water immiscible organic solvent;

treating the levulinic acid composition with an aqueous solution comprising one or more monosaccharides or one or more disaccharides or a mixture of one or more monosaccharides and one or more disaccharides to form a mixture; and partitioning the mixture into an aqueous phase and an organic phase, wherein the acid catalyst in the organic phase is reduced relative to the amount in the levulinic acid composition.

2. The method of paragraph 1, further comprising the step of separating the aqueous phase from the solvent phase.

3. The method of either of paragraphs 1 or 2, wherein the reduction of acid catalyst in the levulinic acid composition after treatment with the aqueous solution is at least two fold.

4. The method of either of paragraphs 1 or 2, wherein the reduction of acid catalyst in the levulinic acid composition after treatment with the aqueous solution is at least ten fold or greater.

5. The method of any of paragraphs 1 or 2, wherein the concentration of acid catalyst that remains in the organic phase is less than 100 ppm.

6. The method of any of paragraphs 1 through 5, wherein the organic solvent is methyl-isobutyl ketone (MIBK), methyl isoamyl ketone (MIAK), cyclohexanone, o, m, and para-cresol, substituted phenols, for example, 2-sec butyl phenol, C4-C18 alcohols, such as n-pentanol, isoamyl alcohol, n-heptanol, 2-ethyl hexanol, n-octanol, 1-nonanol, cyclohexanol, methylene chloride, 1,2-dibutoxy-ethylene glycol, acetophenone, isophorone, o-methoxy-phenol, methyl-tetrahydrofuran, tri-alkylphosphine oxides (C4-C18) and ortho-dichlorobenzene and mixtures thereof or the like, more specifically, methyl isoamyl ketone (MIAK), o, m, and para-cresol, phenol, isoamyl alcohol, n-hexanol, n-heptanol, 2-ethyl hexanol, o-methoxy-phenol, 2-4 dimethyl phenol, methyl isobutyl carbinol, and mixtures thereof or the like, and even more specifically, phenol, all isomers of fluoro, chloro, bromo, and iodo phenols, bis-halogenated phenols, mixtures of halogenated phenols, xylenols, gamma-valerolactone, isoamyl alcohol, neopentyl alcohol, methyl isobutyl carbinol, and mixtures thereof.

7. The method of any of paragraphs 1 through 6, wherein the monosaccharide is glucose, fructose or mixtures thereof and/or the disaccharide is maltose, sucrose or mixtures thereof.

8. The method of any of paragraphs 1 through 7, wherein the concentration of monosaccharide and/or disaccharide present in the aqueous solution is from about 5% to about 80% by weight based on the total weight of the mixture.

9. The method of any of paragraphs 1 through 8, wherein the concentration of acid catalyst present is from about 0.01% to about 5% by weight based on the total weight of the mixture.

10. The method of any of paragraphs 1 through 9, wherein the concentration of levulinic acid present is from about 1% to about 30% by weight based on the total weight of the mixture.

11. The method of any of paragraphs 1 through 10, wherein the acid catalyst is sulfuric acid or hydrochloric acid.

12. A counter current liquid liquid extraction process to prepare a levulinic acid composition substantially without acid catalyst present comprising the steps:

providing a levulinic acid composition comprising levulinic acid, an acid catalyst and a water immiscible organic solvent;

flowing the levulinic acid composition into a bottom inlet of a counter current liquid liquid extractor;

providing an aqueous solution comprising water and one or more monosaccharides or one or more disaccharides or a mixture of one or more monosaccharides and one or more disaccharides;

flowing the aqueous solution into an upper inlet of a counter current liquid liquid extractor; and removing a resultant organic solvent rich extract phase containing levulinic acid with reduced amounts acid catalyst relative to the acid catalyst content of the levulinic acid composition.

13. The method of paragraph 12, wherein the levulinic acid composition was heated from about 25° C. to about 100° C. prior to addition to the counter current liquid liquid extractor.

14. The method of paragraph 12, wherein the feed rate of the levulinic acid composition to aqueous solution is less than 1:1.

15. The method of paragraph 14, wherein the feed rate is about 0.1:1.

16. An extraction process to prepare a levulinic acid composition substantially without acid catalyst present comprising the steps:

providing a levulinic acid composition comprising levulinic acid, an acid catalyst and a water immiscible organic solvent;

flowing the levulinic acid composition into a vessel;

providing an aqueous solution comprising water and one or more monosaccharides or one or more disaccharides or a mixture of one or more monosaccharides and one or more disaccharides;

flowing the aqueous solution into the vessel;

mixing the levulinic acid composition and the aqueous solution to form an emulsion;

allowing the emulsion to separate into two layers, an aqueous phase and an organic phase; and removing a resultant organic solvent phase containing levulinic acid with reduced amounts of acid catalyst relative to the acid catalyst content of the levulinic acid composition.

17. The method of paragraph 16, wherein the process is conducted in a mixer-settler apparatus.

18. The method of any of paragraphs 1 through 17, wherein the aqueous phase and the organic phase are separated by settling, decanting or centrifugation.

19. The method of any of paragraphs 1 through 18, further comprising the steps of purifying the water immiscible organic solvent and recycling the organic solvent back into the extraction process.

20. The method of any of paragraphs 1 through 19, further comprising the step of isolating the levulinic acid from the water immiscible organic solvent.

21. The method of paragraph 20, further comprising the step of purifying the isolated levulinic acid by distillation, crystallization, esterification with an alcohol, or chromatography.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Analytical Measurements.

HPLC was used for measuring LA: The instrument used was a WATERS 2695 LC system with a WATERS 2414 RI detector. An Aminex 87H column (300×7.8 mm) was used with 10 µL injections. An isocratic flow of 0.6 mL/min is used with a mobile phase mixture of 5 mM $H_2SO_4$ in Water (nanopure) and 3% Acetonitrile (HPLC grade). The column temperature was maintained at 50° C. RI detector temperature is 50° C.

Ion Chromatography (IC) was used to determine low levels of sulfuric acid (<100 ppm): Sample prep: Organic phase samples containing <100 ppm sulfuric acid were back-extracted into water and filtered through C18 solid phase extraction cartridge to remove organic acids prior to injection on the IC. System: Dionex ICS-2100 Ion Chromatography System (Thermo Scientific, Inc.). Mobile phase: nano-pure water with 30 mM KOH at 30° C. Flow rate: 1.5 mL/min. Column: Dionex IonPac AS11-HC, 4×250 mm Detection: Suppressed Conductivity Suppressor: Dionex ASRS 300, 4 mm, 112 mA Injection Vol.: 25 uL.

Titration was used for samples containing >100 ppm of sulfuric acid: Aqueous samples and organic samples containing >100 ppm sulfuric acid were diluted in methanol and titrated with 0.02N KOH in methanol to pH 2-3 using Mettler Toledo analyzer (model number DL22) and a pH probe useful for organic and aqueous solutions.

Water was measured using a Karl Fisher Titrator (KF).

GC-FID was used to determine the % of LA condensation products with the solvent, LBX-98®. The molecular weight of the LA-LBX 98® dimer by-products was measured by GC-MS to be =220 g/mol. The molecular weight of the LA-LBX 98® dimer by-products that has been further dehydrated was measured by GC-MS to be =200 g/mol.

All samples were weighed on an analytical balance to 4 decimal places.

EXAMPLES

Examples

Reagent description: LBX-98® Supplier: Merisol, Inc.; Mixture of 66-67% 2,4 xylenol and 30-31% 2,5 xylenol Organic Extract Composition A 11.5% Levulinic Acid (LA)

0.9% Formic Acid (FA)

0.1% Sulfuric Acid (SA)

4.6% Water 82.9% LBX-98® (Merisol, Inc.)

Composition B 11.3% LA 0.9% FA 0.2% SA 4.1% Water
83.5% LBX-98® (Merisol, Inc.)
Sugar Solution
Composition C
Cornsweet® 90 (ADM) in water
2.1% Glucose
17.3% Fructose
80.6% water
Composition D
Glucose mixture in water
18.4% Glucose
81.6% water

Example 1

A 15 mL centrifuge tube was charged with 12 g of Composition A and 1.2 g of Composition C. The centrifuge tube was shaken for 30 seconds to mix the two layers. Sample was centrifuged for 10 minutes to separate the layers. Layers were then separated for analysis by pipetting each layer into separate 20 mL scintillation vials. The contents were weighed on an analytical balance to record the mass of each layer. All steps were done at room temperature (19-23° C.).

Example 2

Same as example 1 but with 12 g of Composition A and 1.8 g Composition C.

Example 3

Same as example 1 but with 12 g Composition A and 2.4 g Composition C.

Example 4

Same as example 1 but with 12 g Composition A and 3.0 g Composition C.

The data for Examples 1-4 is shown in Table 1.

Example 5

Same as example 2.

Example 6

Same as example 3.

The data for Examples 5-6 is shown in Table 2.

Example 7

A 15 mL centrifuge tube was charged with 12 g of Composition B and 1.2 g of Composition D. The centrifuge tube was shaken for 30 seconds to mix the two layers. Sample was centrifuged for 10 minutes to separate the layers. Layers were then separated for analysis. All steps were done at room temperature (19-23° C.).

Example 8

Same as example 7 but with 12 g of Composition B and 1.8 g Composition D.

Example 9

Same as example 7 but with 12 g of Composition B and 2.4 g Composition D.

Example 10

Same as example 7 but with 12 g of Composition B and 3.0 g Composition D.

The data in Examples 7-10 is shown in Table 3.

TABLE 1

|  | Experiment 1 | | Experiment 2 | | Experiment 3 | | Experiment 4 | |
| --- | --- | --- | --- | --- | --- | --- | --- | --- |
| Initial LA:SA (wt:wt) | 115 | | 115 | | 115 | | 115 | |
| Layer | Top | Bottom | Top | Bottom | Top | Bottom | Top | Bottom |
| Layer Weight (g) | 12.7429 | 0.5521 | 12.7724 | 1.1049 | 12.7050 | 1.8165 | 12.8026 | 2.3295 |
| SA (%) | 0.0101 | 1.9602 | 0.0057 | 0.9969 | 0.0036 | 0.7747 | 0.0026 | 0.4949 |
| Final LA:SA (wt:wt) | 1052 | | 1828 | | 2871 | | 3980 | |

TABLE 2

|  | Experiment 5 | | Experiment 6 | |
| --- | --- | --- | --- | --- |
| Initial LA:SA (wt:wt) | 115 | | 115 | |
| Layer | Top | Bottom | Top | Bottom |
| Layer Weight (g) | 12.7655 | 1.0819 | 12.6763 | 1.7085 |
| SA (%) | 0.0076 | 1.0631 | 0.0036 | 0.6923 |
| Final LA:SA (wt:wt) | 1379 | | 2888 | |

TABLE 3

|  | Experiment 7 | | Experiment 8 | | Experiment 9 | | Experiment 10 | |
| --- | --- | --- | --- | --- | --- | --- | --- | --- |
| Initial LA: SA (wt:wt) | 56.5 | | 56.5 | | 56.5 | | 56.5 | |
| Layer | Top | Bottom | Top | Bottom | Top | Bottom | Top | Bottom |
| Layer Weight (g) | 12.5905 | 0.5857 | 12.6804 | 1.1347 | 12.6245 | 1.7281 | 12.6035 | 2.3577 |
| SA (%) | 0.0193 | 3.5190 | 0.0137 | 1.8880 | 0.0103 | 1.2520 | 0.0085 | 0.9050 |
| LA:SA | 570 | | 796 | | 1055 | | 1235 | |

The data in Tables 1-3 shows a novel method for selectively removing sulfuric acid from an organic extraction solvent containing weak acids. The method uses an aqueous sugar solution composed of either glucose or a mixture of glucose and fructose to remove sulfuric acid impurities into the organic extraction solvent. The sulfuric acid is removed selectively from the organic solvent so that the concentration of LA relative to the concentration of sulfuric acid increases by an order of magnitude or more in the organic solvent after one stage of extraction.

General Experimental for Counter-Current Liquid Liquid Extraction in a KARR® Column (KMPS, Inc.)

Compositions E and F were washed with Composition C in order to reduce the sulfuric acid level in Composition E-F solvent rich extract (SRE). Compositions E and F were fed through the bottom feed of the column (Inlet 2, FIG. 1) and the Composition C solution from the top feed (Inlet 2, FIG. 1). Compositions E and F were heated to 60° C. prior to feeding the column and Composition C was at ambient temperature. The feed ratio of Composition C:Composition E (or F) was maintained at 0.1:1, to minimize levulinic acid loss to the Composition C raffinate.

Composition Description of E and F Before Washing with Composition C.

| Component | Composition E | Composition F |
|---|---|---|
| FA (wt %) | 0.64 | 0.95 |
| LA (wt %) | 10.33 | 11.21 |
| Water* (wt %) | 4.5 | 4.5 |
| SA (wt %) | 0.023 | 0.121 |
| LBX-98* (wt %) | 84.5 | 83.2 |

*estimate

The Composition E or F solvent rich extract was fed from the bottom of the column @ 150 lbs/hr (pre-heated to 60° C. using a heat exchanger). The Composition C was fed from the top of the column (Inlet 1, FIG. 1) @ 15 lbs/hr. The agitator speed in the column was set at 150 spm. The sulfuric acid data for the solvent rich extract for two different experiments is summarized in Table 4.

TABLE 4

| Entry | SA pre-wash (ppm) | LA:SA prewash (wt:wt) | SA post wash (ppm) | LA:SA post wash (wt:wt) | SA removed (%) |
|---|---|---|---|---|---|
| Example 11 (Composition E) | 223 | 506 | 43 | 2023 | 80.4 |
| Example 12 (Composition F) | 1210 | 103 | 97 | 907 | 91.6 |

% SA removed=100−100*(X/Y)

X=% sulfuric acid in composition E (or F) solvent rich extract multiplied by the flow rate composition E (or F) solvent rich extract
Y=% sulfuric acid in composition E (or F) multiplied by the flow rate composition E (or F)

Effect of Sulfuric Acid Removal on Levulinic Acid-Solvent By-Products

After extraction, the solvent rich extract is transferred to distillation in order to recover the extraction solvent and isolate levulinic acid. The sugar washed extract (composition E or F solvent rich extract) is collected in a tank and is continuously fed to the distillation columns. The composition of the solvent rich extract fed to distillation can have LA:SA ratio varying from 900-2000 depending on how much sulfuric acid is present in composition E or F. When the solvent rich extract was not subjected to back washing with mono-saccharides the LA:SA was low (<200). Table 5 summarizes the crude product isolated in the bottoms of the distillation tower for two sets of trials with different LA:SA ratio in the solvent rich extract. Comparative Example 1 did not use the method of back-washing the organic solvent with mono-saccharides to remove sulfuric acid impurities prior to distillation. Example 13 used the method for contacting the organic solvent-comprising levulinic acid and sulfuric acid with an aqueous solution (Composition C), as described in Examples 11-12.

TABLE 5

| Component | Comparative Example 1 | Example 13 |
|---|---|---|
| LA:SA in the distillation feed | 164 (single time point taken from continuous operation) | 900-2000 (several samples taken from process) |
| LA in crude in crude product (% by HPLC) | 8.5 | 58.5 |
| LA-LBX-98 ® dimer byproducts in crude product (% by GC-FID) | 46.3 | 7.5 |
| Ratio of LA:LA-LBX-98 ® dimer by-products | 0.18 | 7.8 |

The data in Table 5 shows that by reducing the sulfuric acid level in the solvent rich extract (increasing LA:SA) the formation of levulinic acid-solvent reaction byproducts was reduced by approximately 43 fold, which is more than an order of magnitude improvement.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method to prepare a levulinic acid composition substantially without an acid catalyst present comprising the steps:
    preparing an aqueous levulinic acid composition comprising levulinic acid, an acid catalyst and water;
    combining the aqueous levulinic acid solution with an immiscible organic solvent to form a mixture;
    partitioning the mixture into an aqueous phase and an organic phase; and
    washing the organic phase with an aqueous treatment solution comprising one or more monosaccharides, one or more disaccharides, or a mixture thereof to reduce the acid catalyst content in the organic phase.

2. The method of claim 1, further comprising the step of separating the aqueous phase from the organic phase.

3. The method of claim 1, wherein the reduction of acid catalyst in the levulinic acid composition after treatment with the aqueous treatment solution is at least two fold.

4. The method of claim 1, wherein the reduction of acid catalyst in the levulinic acid composition after treatment with the aqueous treatment solution is at least ten fold or greater.

5. The method of claim 1, wherein the concentration of acid catalyst that remains in the organic phase is less than 100 ppm.

6. The method of claim 1, wherein the organic solvent is methyl-isobutyl ketone (MIBK), methyl isoamyl ketone (MIAK), cyclohexanone, o, m, and para-cresol, substituted phenols, for example, 2-sec butyl phenol, C4-C18 alcohols, such as n-pentanol, isoamyl alcohol, n-heptanol, 2-ethyl hexanol, n-octanol, 1-nonanol, cyclohexanol, methylene chloride, 1,2-dibutoxy-ethylene glycol, acetophenone, isophorone, o-methoxy-phenol, methyl-tetrahydrofuran, trialkylphosphine oxides (C4-C18) and ortho-dichlorobenzene and mixtures thereof or the like, more specifically, methyl isoamyl ketone (MIAK), o, m, and para-cresol, phenol, isoamyl alcohol, n-hexanol, n-heptanol, 2-ethyl hexanol, o-methoxy-phenol, 2-4 dimethyl phenol, methyl isobutyl carbinol, and mixtures thereof or the like, and even more specifically, phenol, all isomers of fluoro, chloro, bromo, and iodo phenols, bis-halogenated phenols, mixtures of halogenated phenols, xylenols, gamma-valerolactone, isoamyl alcohol, neopentyl alcohol, methyl isobutyl carbinol, and mixtures thereof.

7. The method of claim 1, wherein the monosaccharide is glucose, fructose or mixtures thereof and/or the disaccharide is maltose, sucrose or mixtures thereof.

8. The method of claim 1, wherein the concentration of monosaccharide and/or disaccharide present in the aqueous solution is from about 5% to about 80% by weight based on the total weight of the mixture.

9. The method of any of claims 1 through 8, wherein the concentration of acid catalyst present is from about 0.01% to about 5% by weight based on the total weight of the mixture.

10. The method of claim 1, wherein the concentration of levulinic acid present is from about 1% to about 30% by weight based on the total weight of the mixture.

11. The method of claim 1, wherein the acid catalyst is sulfuric acid or hydrochloric acid.

* * * * *